United States Patent [19]

Ishida et al.

[11] Patent Number: 4,594,004
[45] Date of Patent: Jun. 10, 1986

[54] CONTINUOUS PARTICULATE-MEASURING APPARATUS USING AN OPTOACOUSTIC EFFECT

[75] Inventors: Kozo Ishida; Junji Okayama; Kunio Otsuki, all of Kyoto, Japan

[73] Assignee: Horiba, Ltd., Kyoto, Japan

[21] Appl. No.: 509,229

[22] Filed: Jun. 28, 1983

[30] Foreign Application Priority Data

Jul. 3, 1982 [JP] Japan .................... 57-116444

[51] Int. Cl.$^4$ ........................... G01N 21/61
[52] U.S. Cl. ........................ 356/433; 73/24
[58] Field of Search ......... 356/432, 433, 435, 436, 356/437, 438; 250/345, 350, 351; 73/24, 579

[56] References Cited

U.S. PATENT DOCUMENTS 3,948,345  4/1976  Rosencwaig .................. 356/432
4,277,179  7/1981  Bruce ............................ 356/439

FOREIGN PATENT DOCUMENTS 2059574  4/1981  United Kingdom ............. 356/435

Primary Examiner—R. A. Rosenberger
Attorney, Agent, or Firm—Wenderoth, Lind & Ponack

[57] ABSTRACT

An apparatus for continuously measuring the concentration of particulates in a sample gas by using an optoacoustic effect. Identical laser rays are directed along two optical paths, and a chopper and an optoacoustic cell are position in the recited order in each of the optical paths. Sample gas containing particulates is introduced into one optoacoustic cell and sample gas from which the particulates have been removed is introduced into the other optoacoustic cell. The respective choppers are driven for producing a chopping action on the respective laser rays at a frequency corresponding to the resonant frequency of the corresponding optoacoustic cells, and the outputs from the cells can be compared for providing an indication of the concentration of the particulates in the sample gas.

3 Claims, 3 Drawing Figures

CONTINUOUS PARTICULATE-MEASURING APPARATUS USING AN OPTOACOUSTIC EFFECT

BACKGROUND OF THE INVENTION

The present invention relates to an apparatus for continuous measurements of particulates in a gas by using an optoacoustic effect.

BACKGROUND OF THE INVENTION AND PRIOR ART

It is important in many technological areas to be able to determine the particulate content of a gas such as smoke. One use of such an apparatus is for measuring the concentration of particulates in an exhaust gas from a motor vehicle or the like.

It is known that when light rays are directed into a cell containing gas with particulates therein, there is absorption of rays by said particulates and a resulting heating of said particulates. The particulates can be heated to a greater or lesser extent in accordance with modulation of the rays by a chopper, whereby a change in pressure is produced inside said cell. The concentration of particulates can be quantitatively measured without delay by detecting this change in pressure by means of a microphone. An optoacoustic effect, which is based on such a principle, has been made pratical due to the ability to produce laser rays. It is, however, impossible to correctly measure the amounts of particulates in a sample gase by merely detecting the change in pressure inside a cell resulting from the incidence of chopped laser rays on the single cell since interfering ingredients, which absorb laser rays and also produce a change in pressure, such as $C_3H_8$ and $CO_2$, may be contained in the sample gas.

An attempt has been made to eliminate the interference owing to said interfering ingredients by the apparatus as shown in FIG. 1, in which a chopper 3 and two optoacoustic cells 4 and 5 are arranged in series in an optical path 2 along which laser rays radiated from a source 1 of laser rays are passed, the sample gas containing particulates being introduced into one cell 5 while the same sample gas from which the particulates have been removed is introduced into another cell 4, the influence due to said interfering ingredients being eliminated by subtracting the signal detected by means of a microphone 6 provided in said cell 4 from the acoustic signal detected by means of a microphone 7 provided in said cell 5, and the concentration of particulates being measured by means of the difference signal. The particulates are removed by a filter 8 for removing only particulates, the sample gas containing particulates being introduced into said optoacoustic cell 5 and then being caused to flow into said optoacoustic cell 4 after the particulates contained in the gas have been removed by means of said filter 8.

In order to detect the acoustic pressure accurately by means of said microphones 6 and 7, it is, however necessary that the acoustic pressure in the cells be highest at the positions where said microphones 6 and 7 are positioned. To this end it is necessary for the change in pressure inside each cell 4 and 5 to produce standing waves having the frequencies of the fundamental mode of each cell, i.e. the pressure frequency, or multiples thereof. And to this end it is necessary for the chopping frequency of said chopper 3 to be equal to the frequencies which produce said fundamental mode or the multiples thereof, that is to say the resonance frequency.

The present inventors believe, however, that the resonance frequency and the acoustic pressure-frequency characteristics of one cell 4 can hardly be exactly the same as those of another cell 5. They vary, depending upon the composition of the sample gas, the pressure inside the cells and the like. Consequently, in an apparatus as described above, it is impossible to correctly and accurately measure the concentration of the particulates since the chopping frequency in said cell 4 is the same as that for said cell 5, and the change in acoustic pressure characteristics of said cell 4 resulting from the change in pressure in said cell 4 may be substantially different from that in said cell 5. The reason for the above described differences will be described in detail below.

The resonance frequency $\omega_o$, which produces a standing acoustic wave of the fundamental mode frequency in the cells, is expressed by the following equation:

$$\omega_o = \frac{1}{2l} \sqrt{\frac{\gamma P_o}{\rho_o}}$$

wherein $l$ denotes the length of the cell, $P_o$ denotes the pressure inside the cell, $\rho_o$ denotes the density of the fluid passing through the cell, and $\gamma$ denotes the ratio of specific heats. It can be seen from this formula why the resonance frequency and the acoustic pressure frequency characteristics of said cell 4 are not equal to those of said cell 5, namely because even though the length $l$ of said cell 5, through which the sample gas containing particulates is passed, is equal to the length of said cell 4, through which the sample gas containing no particulates is passed, all of the factors $P_o$, $\rho_o$ and $\gamma$ for said cell 5 are different from those for said cell 4. In general, the acoustic pressure is substantially reduced with a change in said chopping frequency from said resonance frequency, as shown in FIG. 2. For example, the curve ①  in FIG. 2 shows the acoustic pressure-frequency characteristics of the sample gas A passing through said cell 5 while the curve ② in FIG. 2 shows the acoustic pressure-frequency characteristics of the sample gas, from which particulates have been removed, passing through said cell 4. $\omega_1$ denotes the resonance frequency for the sample gas A passing through said cell 5 and $\omega_2$ denotes the resonance frequency for the sample gas, from which particulates have been removed, passing through said cell 4. Whereas the true measure of the particulate concentration is $\Delta P_o$, at a chopping frequency $\omega_1$, the pressure difference appears as $\Delta P$ while at a chopping frequency $\omega_2$, the pressure difference appears to be almost nonexistent.

Moreover, the resonance frequencies for said cells 4 and 5 do not always remain $\omega_1$ and $\omega_2$, respectively, but vary in the neighborhood of $\omega_1$ and $\omega_2$ respectively, so that the acoustic pressure-frequency characteristics vary. For example for a sample gas B, which has the same concentration of particulates and in which the influence of the interference ingredients is the same as in a sample gas A, but the acoustic pressure-frequency characteristics curves ①' and ②' (refer to FIG. 2) of which are slightly shifted rightward from the positions of said curves ① and ②, when the concentration of particulates is measured with the chopping frequency set to $\omega_1$, the pressure difference signal representative of the concentration of particulates becomes $\Delta P'$ as compared to $\Delta P$ for the sample gas A. That is to say, the pressure difference signal for the sample gas B is larger than that for the sample gas A even though the concentration of particulates is identical. This is because even though the output frequency for the same gas B in said cell 5 set to the resonance frequency $\omega_1$ for the sample gas A is only slightly less than that for the sample gas A, the output frequency for the sample gas B in said cell 4 is considerably less than that for the sample gas A. That is to say, the change in output at the chopping frequency in the neighborhood of the resonance frequency is small but it is large at frequencies away from the resonance frequency. Thus it cannot be said that the concentration of particulates can be correctly measured when the chopping frequency is set to the resonance frequency $\omega_1$ of said cell 5. The same is true when the chopping frequency is set to the resonance frequency between $\omega_1$ and $\omega_2$.

SUMMARY OF THE INVENTION

It is an object of the present invention to provide an apparatus in which the laser ray introduced into each cell can be chopped with a frequency corresponding to the resonant frequency inherent in each cell, whereby the concentration of particulates in the sample gas can be correctly measured.

The present invention achieves this object by providing a continuous particulate measuring apparatus using an optoacoustic effect, in which two optical paths of laser rays are formed, a chopper and an optoacoustic cell being arranged in each optical path, the gas containing particulates being introduced into one cell and the gas, from which the particulates have been removed, is introduced into the other optoacoustic cell, and each chopper carrying out the chopping action at the resonant frequency inherent in the optoacoustic cell arranged in the optical path of that chopper.

DESCRIPTION OF THE PREFERRED EMBODIMENT

Figure 3:
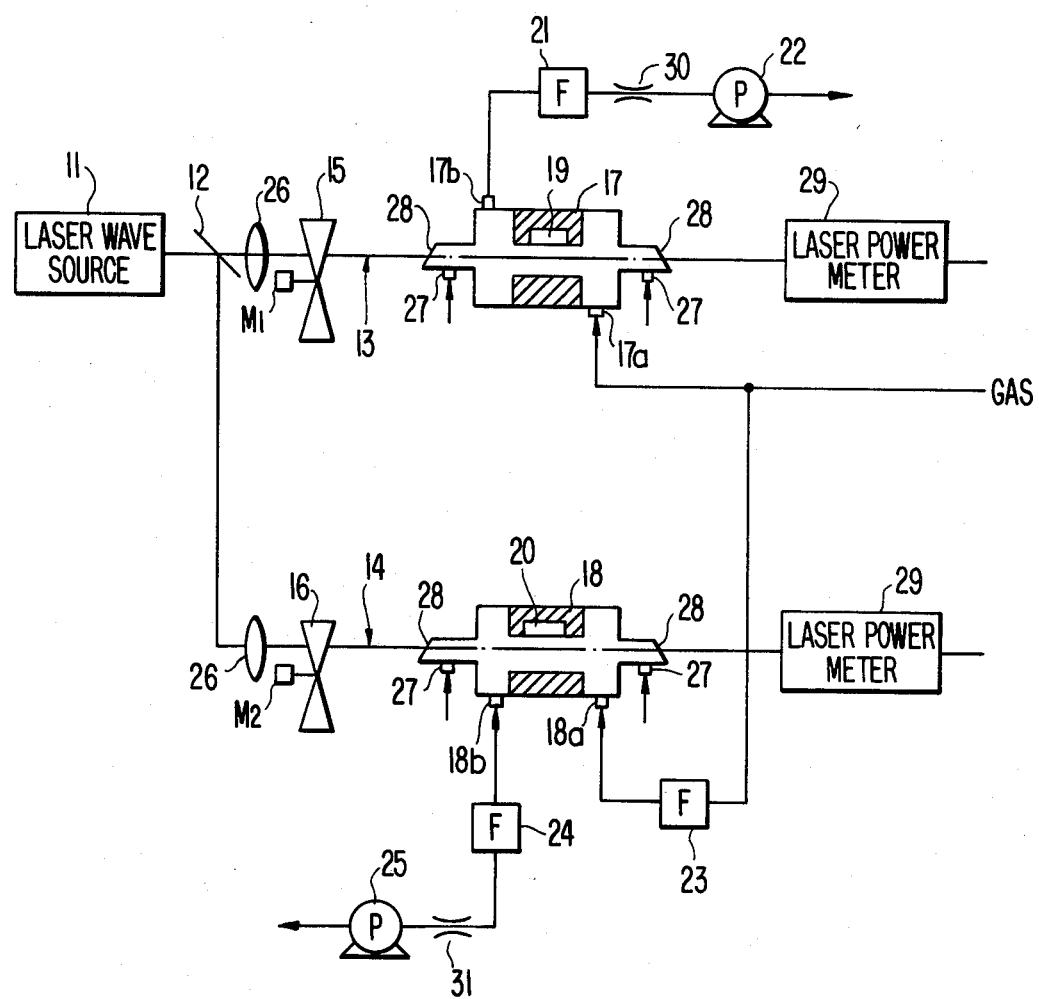
FIG. 3 is a schematic diagram of a preferred embodiment of the present invention.

The preferred embodiment of the present invention will be described below with reference to FIG. 3. Identical laser rays are radiated along two optical paths, e.g. by emitting them from a source 11 of laser rays and dividing the emitted rays into two optical paths 13 and 14 by means of a beam-splitter 12. Said two optical paths 13 and 14 may be formed from two lengths of optical fiber instead of using said beam-splitter 12 or the rays can be radiated along the two paths by using two sources of laser rays. Choppers 15 and 16 and optoacoustic cells 17 and 18 are arranged in the respective optical paths 13 and 14. Although an open-tube type cell open at both ends thereof is used for said cells 17 and 18 in the preferred embodiment shown, a closed-tube type cell closed at one end thereof may be used instead. The cells include microphones 19 and 20 arranged at the central portion of the respective cells 17 and 18 in order to detect the highest acoustic pressure therein, A part of a sample gas, which contains particulates, is introduced into one cell 17 through an inlet 17a and is exhausted from an outlet 17b therein, and then passed through a filter 21 and a Venturi tube 30 by means of a first pump 22. Said filter 21 also prevents said microphone 19 from picking up the noises of said pump 22. The remainder of the gas is directed through a filter 23 for removing particulates and is introduced into the other cell 18 through an inlet 18a and is exhausted therefrom through an outlet 18b and then passed through a filter 24 and a Venturi tube 31 by means of a second pump 25. Said filter 24 acts in the same manner as said filter 21.

Said choppers 15 and 16 are driven by means of, for example, DC motors $M_1$ and $M_2$ and the chopping frequency can be changed by adjusting the respective DC voltages of the current supplied to said motors.

Figure 1:
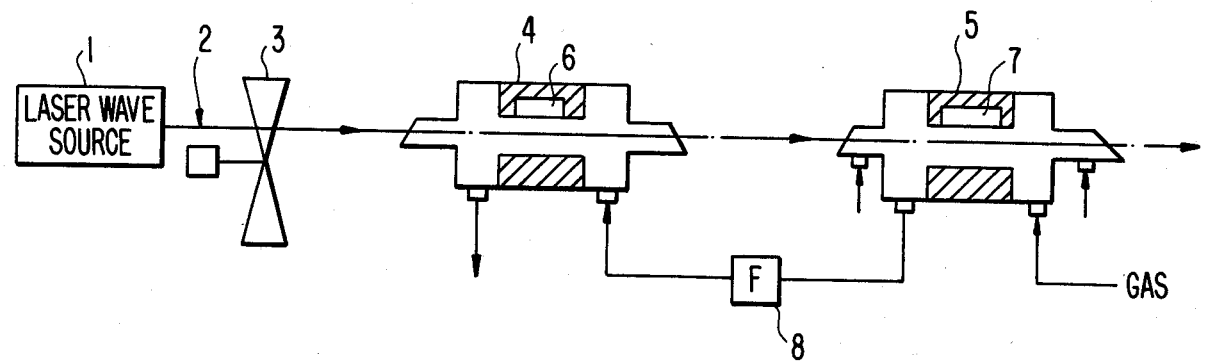
FIG. 1, is a schematic diagram of a conventional continuous particulate-measuring apparatus.
Figure 2:
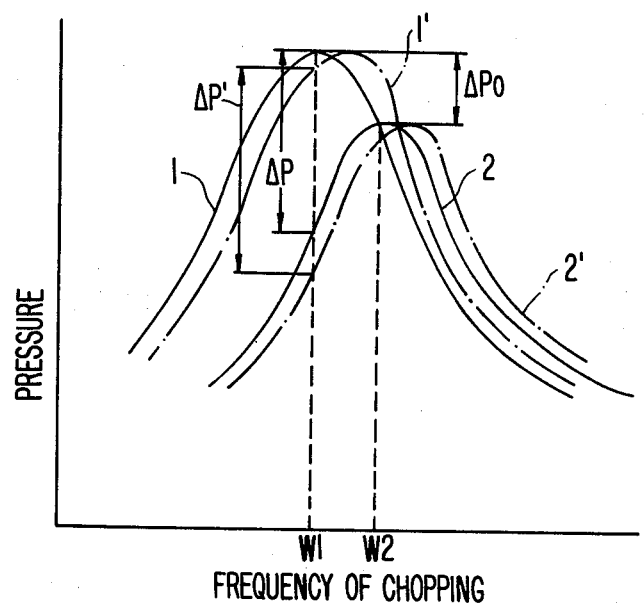
FIG. 2 is a graph showing the relation between the chopping frequencies and the changes in acoustic pressure for each cell.

The chopping frequency of the one chopper 15 is set to the resonance frequency of said cell 17 arranged in said optical path 13, in which said chopper 15 is also arranged, while the chopping frequency of the other chopper 16 is set to the resonance frequency of said cell 18 arranged in said optical path 14, in which said chopper 16 is also arranged. Thus, referring to the diagram shown in FIG. 2, the chopping frequency of said chopper 15 is set to $\omega_1$ and the chopping frequency of said chopper 16 is set to $\omega_2$. The chopping frequencies are set to $\omega_1$ and $\omega_2$ generally by adjusting the rotational frequency of said choppers 15 and 16 until the outputs of the respective microphones 19 and 20 are the highest. It is however, not necessary to change the rotational frequency of the choppers over a very wide range since the resonance frequency can be approximately calculated by the equation given hereinbefore.

According to the above described construction, laser rays introduced into said cells 17 and 18 are chopped at the resonance frequency of the corresponding cell. Accordingly, the fundamental mode of sound (or multiples thereof) is formed inside said cells 17 and 18, and the difference between the output of said microphone 19 arranged inside said cell 17 and the output of said microphone 20 arranged inside said cell 18 corresponds exactly to $\Delta P_o$ shown in FIG. 2. Thus just the concentration of the particulates can be correctly measured because the influence of the interfering ingredients has been eliminated from said $\Delta P_o$. Further, it is preferable to use as said microphones 19 and 20 microphones having frequency characteristics which are most sensitive in the neighborhood of resonance frequency of the respective cells. Moreover, it is better to select as said microphones 19 and 20 microphones which have a low sensitivity to the background sounds, so as not to pick up these sounds. Referring again to FIG. 3, lenses 26 are provided for collecting the laser rays. Inlets 27 can be provided in cells 17 and 18 for purge air. A Brewster's window 28 is provided in each cell, and a laser power meter 29 is provided in the optical paths downstream of each.

As described above in the apparatus for continuous measurement of particulates according to the present invention, laser rays introduced into two optoacoustic cells are chopped at resonance frequencies of the respective cells, whereby the fundamental vibration mode or multiples are formed inside each cell, and thus the output at the frequency, at which the acoustic pressure is highest, can be obtained from the microphones in the respective cells. Accordingly, the concentration of just the particulates can be measured from the difference between the acoustic pressure detected by one microphone and the acoustic pressure detected by another microphone. Further, even though the length of one cell is somewhat different from the length of the other cell, the chopping of the laser rays can be made corresponding to the resonance frequency of each cell by individually adjusting the chopping frequency of the choppers arranged in the respective optical paths. Consequently, any difference in the length of the respective cells does not have any influence upon the accuracy of measurement. Thus the cell can be comparatively easily manufactured.

What is claimed is:

1. An apparatus for continuously measuring the concentration of particulates in a sample gas by using an optoacoustic effect, comprising:

means for directing identical laser rays along two optical paths;

a chopper and an optoaboustic cell positioned in the recited order in each of said optical paths downstream of said means;

a gas introducing means for introducing sample gas containing particulates into one optoacoustic cell and for introducing the sample gas from which the particulates have been removed into the other optoacoustic cell; and chopper drive means connected to said choppers for driving the respective choppers for producing a chopping action on the respective laser rays at a frequency corresponding to the resonant frequency of the corresponding optoacoustic cells, whereby the outputs from the cells can be compared for providing an indication of the concentration of the particulates in the sample gas.

2. An apparatus as claimed in claim 1 wherein each cell has an inlet and an outlet, and said gas introducing means is connected to said inlet, and said apparatus further comprises a pump connected with the outlet of each optoacoustic cell and a gas filter between each pump and the outlet of the corresponding cell.

3. As apparatus as claimed in claim 1 in which said cells are each an open tube type cell, and said apparatus further comprises a laser power meter downstream of each cell for detecting the power of the laser ray after it has passed through the cell.

* * * * *